(12) United States Patent
Vitale et al.

(10) Patent No.: US 12,653,434 B2
(45) Date of Patent: Jun. 16, 2026

(54) CONDUCTIVE HYDROGEL-BASED WEARABLE HEALTH MONITORS

(71) Applicant: The Trustees of the University of Pennsylvania, Philadelphia, PA (US)

(72) Inventors: Flavia Vitale, Wilmington, DE (US); Shu Yang, Blue Bell, PA (US); Mehrnaz Mojtabavi, Horsham, PA (US); Brendan Murphy, Bala Cynwyd, PA (US); Mingtao Chen, Philadelphia, PA (US); Baohong Chen, Philadelphia, PA (US); Yuchong Gao, Philadelphia, PA (US)

(73) Assignees: The Trustees of the University of Pennsylvania, Philadelphia, PA (US); The United States Government as Represented by The Department of Veterans Affairs, Washington, DC (US)

( * ) Notice: Subject to any disclaimer, the term of this patent is extended or adjusted under 35 U.S.C. 154(b) by 347 days.

(21) Appl. No.: 18/323,592

(22) Filed: May 25, 2023

(65) Prior Publication Data

US 2023/0397870 A1 Dec. 14, 2023

Related U.S. Application Data

(60) Provisional application No. 63/365,284, filed on May 25, 2022.

(51) Int. Cl.
*A61B 5/259* (2021.01)
*A61B 5/24* (2021.01)
(Continued)

(52) U.S. Cl.
CPC ............ *A61B 5/259* (2021.01); *A61B 5/2415* (2021.01); *A61B 5/266* (2021.01);
(Continued)

(58) Field of Classification Search
CPC ......... A61B 5/259; A61B 5/263; A61B 5/266; A61B 5/268; A61B 5/291; A61L 24/0031;
(Continued)

(56) References Cited

U.S. PATENT DOCUMENTS 5,686,180 A 11/1997 Rivlin et al.
2012/0182693 A1 7/2012 Boday et al.
(Continued)

FOREIGN PATENT DOCUMENTS

CN 103359368 A 10/2013
CN 112457501 A 3/2021
(Continued)

OTHER PUBLICATIONS

Brooks et al., "Synthesis and applications of boronic acid-containing polymers: From Materials to Medicine", Chem., Rev., 2016, vol. 116 No. 3, pp. 1375-1397.
(Continued)

*Primary Examiner* — Eun Hwa Kim

(74) *Attorney, Agent, or Firm* — BakerHostetler

(57) ABSTRACT

A health monitor, comprising: an electrode that includes a hydrogel composition comprising a first network that comprises at least two hydroxyl-bearing chains of a first polymer, the at least two hydroxyl-bearing polymer chains being crosslinked by crosslinks that comprise one or more boronic ester bonds; and at least one conductive additive dispersed within the composition, the electrode being configured for patient contact. Also provided are related methods.

25 Claims, 6 Drawing Sheets

AB₁₅C₂ hydrogel    MXene addition    Kneading    Composite

(51) Int. Cl.
| | |
|---|---|
| *A61B 5/266* | (2021.01) |
| *A61L 24/00* | (2006.01) |
| *A61L 24/04* | (2006.01) |
| *C08J 3/075* | (2006.01) |
| *C08K 3/013* | (2018.01) |
| *C08K 5/00* | (2006.01) |

(52) U.S. Cl.
CPC ....... *A61L 24/0031* (2013.01); *A61L 24/0094* (2013.01); *A61L 24/046* (2013.01); *C08J 3/075* (2013.01); *C08J 2329/04* (2013.01); *C08K 3/013* (2018.01); *C08K 5/0008* (2013.01); *C08K 2201/001* (2013.01)

(58) Field of Classification Search
CPC .. A61L 24/0094; A61L 24/0046; C08J 3/075; C08J 2329/04; C08K 3/013; C08K 5/0008; C08K 2201/001
See application file for complete search history.

(56) References Cited

U.S. PATENT DOCUMENTS

| | | | |
|---|---|---|---|
| 2021/0380848 A1 | 12/2021 | Zhao et al. | |
| 2022/0160281 A1* | 5/2022 | Hatakeyama | ..... C08F 220/1809 |
| 2023/0109620 A1 | 4/2023 | Niimi et al. | |

FOREIGN PATENT DOCUMENTS

| | | | | | |
|---|---|---|---|---|---|
| CN | 112646209 A | * | 4/2021 | ................ | C08J 3/24 |
| CN | 113292671 A | | 8/2021 | | |
| EP | 3878891 A1 | * | 9/2021 | ................ | C08L 5/08 |
| WO | WO-2013127989 A1 | * | 9/2013 | .............. | C08L 95/00 |
| WO | 2020/160463 A1 | | 8/2020 | | |
| WO | 2023/097097 A1 | | 6/2023 | | |

OTHER PUBLICATIONS

Cash et al., "Room-temperature self-healing polymers based on dynamic-covalent boronic esters," Macromolecules, 2015, vol. 48, No. 7, pp. 2098-2106.

Chen et al., "Hydrogel with ultrafast self-healing property both in air and underwater," ACS Applied Materials & Interfaces, 2018, vol. 10, No. 1, pp. 1258-1265.

Chen et al., "Novel design strategy for fully physically linked double network hydrogels with tough, resistant and self-healing properties", Adv. Funct. Mater., 2015, vol. 25 No. 10, pp. 1598-1607.

Cromwell et al., "Malleable and self-healing covalent polymer networks through tunable dynamic boronic easter bonds," Journal of the American Chemical Society, 2015, vol. 137, No. 20, pp. 6492-6495.

Du et al., "Fabrication of poly(vinyl alcohol)/Sodium alginate hydrogel beads and its application in photo-fenton degradation of tetracycline", j. mater., Sci., 202, vol. 56 No. 1, pp. 913-926.

Dydo et al., "Chapter 11—Boron Removal Using Ion Exchange Membranes," in Boron Separation Processes, Amsterdam, 2015, pp. 249-265.

Gong et al., "Double-network hydrogels with extremely high mechanical strength", Adv. Mater., 2003, vol. 15 No. 14, pp. 1155-1158.

He et al., "Responsive self-healing hydrogels formed by boronate-catechol complexation", Chem. Commun., 2011, vol. 47 No. 26, pp. 7497-7499.

Kathan et al., "Control of imine exchange kinetics with photoswitches to modulate self-healing n polysiloxane networks by light illumination", Angew. Chem., Int. Ed., 2016, vol. 55 No. 44, pp. 13882-13886.

Konieczynska et al., "On-demand dissolution of a dendritic hydrogel-based dressing for second-degree burn wounds through thiol-thioester exchange reaction", Angew. Chem., Int. Ed., 2016, vol. 55 No. 34, pp. 9984-9987.

Lai et al., "A still and healable polymer based on dynamic-covalent boroxine bonds," Advanced Materials, 2016, vol. 28, No. 37, pp. 8277-8282.

Lai et al., "Colorless, transparent, robust and fast scratch-self healing elastomers via a phase-locked dynamic bonds design," Advanced Materials, 2018, vol. 30, No. 38, Article 1802556.

Li et al., "Organic-Inorganic hierarchical self-assembly into robust luminescent supramolecular hydrogel," Advanced Functional Materials, 2017, vol. 27, No. 2, Article 1604379.

Liu et al., "Electrically conductive nanocomposite hydrogels embedded with functionalized carbon nanotubes for spinal cord injury," New Journal of Chemistry, 2018, vol. 42, No. 21, pp. 17671-17681.

Melo et al., "Synthesis and characterization of Poly(Vinyl Alcohol)-Boric Acid Beads from PVA with several hydrolysis degrees," e-Polymers, 2007, vol. 7.

Nakahata et al., "Redox-responsive self-healing materials formed from host-guest polymers," Nature Communications, 2011, vol. 2, Article 511.

Ogden et al., "Recyclable, strong and highly malleable thermosets based on boroxine networks," Journal of the American Chemical Society, 2018, vol. 140, No. 20, pp. 6217-6220.

Rottger et al., "High-Performance Vitrimers from commodity thermoplastics through dioxaborolane metathesis," Science, 2017, vol. 356, No. 6333, pp. 62-65.

Yang et al., "Making and remaking dynamic 3D structures by shining light on flat liquid crystalline vitrimer films without a mold," Journal of the American Chemical Society, 2016, vol. 138, No. 7, pp. 2118-2121.

Yuk et al., "Rapid and coagulation-independent haemostatic sealing by a paste inspired by barnacle glue," Nature Biomedical Engineering, 2021, vol. 5, No. 10, pp. 1131-1142.

Zhao et al., "A tough and self-healing polymer enabled by promoting bond exchange in boronic esters with neighboring hydroxyl groups," ACS Materials Letters, 2021, vol. 3, No. 9, pp. 1328-1338.

Zheng et al., "A surprise from 1954: Siloxane equilibration is a simple, robust, and obvious polymer self-healing mechanism," Journal of the American Chemical Society, 2012, vol. 134, No. 4, pp. 2024-2027.

Chakma et al., "Dynamic Covalent Bonds in Polymeric Materials", Angew. Chem. Int. Ed., 2019, vol. 58, No. 29, pp. 9682-9695.

Ershad et al., "Ultra-conformal drawn-on-skin electronics for multifunctional motion artifact-free sensing and point-of-care treatment", Nat. Commun., 2020, vol. 11, Article No. 3823, pp. 1-13.

Kim et al., "Fracture, Fatigue and Friction of Polymers in Which Entanglements Greatly Outnumber Cross-Links", Science, 2021, vol. 374, No. 6564, pp. 212-216.

Li et al., "Designing Hydrogels for Controlled Drug Delivery", Nature Reviews Materials, 2016, vol. 1, No. 12, 16071, pp. 1-17.

Liao et al., "Polyvinyl Alcohol-Stabilized Liquid Metal Hydrogel for Wearable Transient Epidermal", Sensors Adv. Funct. Mater., 2019, vol. 11, pp. 47358-47364.

Liu et al., "Genome editing with CRISPR-Cas nucleases, base editors, transposases and prime editors", Nature Biotechnology, 2020, vol. 38, No. 7, pp. 824-844.

Liu et al., "Soft and elastic hydrogel-based microelectronics for localized low-voltage neuromodulation", Nature Biomedical Engineering, 2019, vol. 3, pp. 58-68.

Sempionatto et al., "An epidermal patch for the simultaneous monitoring of haemodynamic and metabolic biomarkers", Nat. Biomed. Eng., 2021, vol. 5, pp. 737-748.

South et al., "Autonomic Self-Healing of Hydrogel Thin Films", Angew. Chem. Int. Ed., 2010, vol. 49, No. 4, pp. 767-771.

Sun et al., "Highly Stretchable and Tough Hydrogels", Nature, 2012, vol. 489, No. 7414, pp. 133-136.

Tringides et al., "Viscoelastic surface electrode arrays to interface with viscoelastic tissues", Nat. Nanotech, 2021, vol. 16, No. 9, pp. 1019-1029.

Wang et al., "Green and Facile Synthesis of Bio-Based, Flame-Retardant, Latent Imidazole Curing Agent for Single-Component Epoxy Resin", J. Appl. Polym. Sci., 2022, vol. 4, pp. 3564-3574.

Yang et al., "A laser-engraved wearable sensor for sensitive detection of uric acid and tyrosine in sweat", Nat. Biotechnol., 2020, pp. 1-48.

(56) References Cited

OTHER PUBLICATIONS

Zhang et al., "Dual base editor catalyzes both cytosine and adenine base conversions in human cells", Chem. Soc. Rev., 2020, vol. 38, No. 7, pp. 856-860.

Zhang et al., "MXenes stretch hydrogel sensor performance to new limits", Sci., Advances, Jun. 15, 2018, vol. 4, No. eaat0098, pp. 1-8.

Advanced Wound Care Market Size, Share & Trends Analysis Report by Product, Report Id: GVR-4-68038-186-3, Published Date, Mar. 2021.

Ailincai et al., "Polyvinyl Alcohol Boric Acid—a Promising Tool for the Development of Sustained Release Drug Delivery Systems", Mater. Sci. Eng. C . 2020, vol. 107, 110316, pp. 1-11.

Arzt et al., "From Micro to Nano Contacts in Biological Attachment Devices", Proc. Natl. Acad. Sci. 2003, vol. 100, No. 19, pp. 10603-10606.

Bapat et al., "Dynamic-Covalent Macromolecular Stars with Boronic Ester Linkages", J. Am. Chem. Soc. 2011, vol. 133, No. 49, pp. 19832-19838.

Belowich et al., "Dynamic Imine Chemistry", Chem. Soc. Rev. 2012, vol. 41 No. 6, pp. 2003-2024.

Bovone et al., "Engineering Hydrogel Adhesion for Biomedical Applications via Chemical Design of the Junction", ACS Biomater. Sci. Eng. 2021, vol. 7, pp. 4048-4076.

Chakma et al., "Anilinium Salts in Polymer Networks for Materials with Mechanical Stability and Mild Thermally Induced Dynamic Properties", ACS Macro Lett. 2019, vol. 8 No. 2, pp. 95-100.

Chen et al., "A Thermally Re-Mendable Cross-Linked Polymeric Material", Science 2002, vol. 295 No. 5560, pp. 1698-1702.

Chen et al., "Fast, reversible and biocompatible wound dressing adhesives with dynamic covalent bonds", Materials Science and Engineering, University of Pennsylvania, 2021, 16 pages.

Chen et al., "Fast, strong, and reversible adhesives with dynamic covalent bonds for potential use in wound dressing", Jun. 2, 2022, vol. 119, No. 29, pp. 9.

Cho et al., "Intrinsically Reversible Superglues Via Shape Adaptation Inspired by Snail Epiphragm", Proc. Natl. Acad. Sci. 2019, vol. 116 No. 28, pp. 13774-13779.

Ethicon Dermabond Skin Closure System. https://www.jnjmedicaldevices.com/enUS/product/dermabond-prineo-skin-closure-system, Retreived on Jun. 20, 2024, pp. 1-12.

Foster et al., "Effect of Polymer Network Architecture, Enhancing Soft Materials Using Orthogonal Dynamic Bonds in an Interpenetrating Network", ACS Macro Lett. 2017, vol. 6 No. 5, pp. 495-499.

Gadhave et al., "Effect of Addition of Boric Acid on Thermo-Mechanical Properties of Microcrystalline Cellulose/ Polyvinyl Alcohol Blend and Applicability as Wood Adhesive", J. Adhes. Sci. Technol., 2021, vol. 35 No. 10, 1072-1086.

Gao et al., "Hydrogel-Mesh Composite for Wound Closure", Proc. Natl. Acad. Sci. 2021, vol. 118 No. 28, e2103457118, pp. 1-6.

Han et al., "Self-Hydrophobization in a Dynamic Hydrogel for Creating Nonspecific Repeatable Underwater Adhesion", Adv. Funct. Mater. 2020, vol. 30 No. 7, 1907064, pp. 1-9.

He et al., "Toward Self-Healing Hydrogels Using One-Pot Thiol-Ene Click and Borax-Diol Chemistry", ACS Macro Lett. 2015, vol. 4 No. 7, pp. 673-678.

Hensel et al., "Engineering Micropatterned Dry Adhesives: From Contact Theory to Handling Applications", Adv. Funct. Mater. 2018, vol. 28 No. 28, 1800865, pp. 1-15.

Jenkins et al., "Integrating Mussel Chemistry into a Bio-Based Polymer to Create Degradable Adhesives", Macromolecules 2017, vol. 50 No. 2, pp. 561-568.

Kane, "Polyvinyl Alcohol Adhesives Containing Boric Acid and Hexamethylenetetramine or Triethylenediamine as Additive to Impart Quick Tack", US3320200A, 1965.

Kim et al., "Drawing-Based Manufacturing of Shear-Activated Reversible Adhesives", ACS Appl. Mater. Interfaces 2020, vol. 12 No. 17, pp. 20075-20083.

Kinloch, "The Science of Adhesion", J. Mater. Sci. 1980, vol. 15 No. 9, pp. 2141-2166.

Li et al., "Tough Adhesives for Diverse Wet Surfaces", Science 2017, vol. 357 No. 6349, pp. 378-381.

Meng et al., "Ph- and Sugar-Induced Shape Memory Hydrogel Based on Reversible Phenylboronic Acid-Diol Ester Bonds. Macromol", Rapid Commun. 2015, vol. 36 No. 6, pp. 533-537.

Montarnal et al., "Silica-Like Malleable Materials from Permanent Organic Networks", Science 2011, vol. 334, No. 6058, pp. 965-968.

Obadia et al., "Reprocessing and Recycling of Highly Cross-Linked Ion-Conducting Networks through Transalkylation Exchanges of C-N Bonds", J. Am. Chem. Soc. 2015, vol. 137 No. 18, pp. 6078-6083.

Obadia et al., "Tuning the Viscosity Profile of Ionic Vitrimers Incorporating 1,2,3-Triazolium Cross-Links", Adv. Funct. Mater. 2017, vol. 27 No. 45, 1703258, pp. 1-10.

Osthoff et al., "Chemical Stress-Relaxation of Polydimethylsiloxane Elastomers", J. Am. Chem. Soc. 1954, vol. 76 No. 18, pp. 4659-4663.

Rekondo et al., "Catalyst-Free Room-Temperature Self-Healing Elastomers Based on Aromatic Disulfide Metathesis", Mater. Horiz. 2014, vol. 1 No. 2, pp. 237-240.

Rose et al., "Nanoparticle Solutions as Adhesives for Gels and Biological Tissues", Nature 2014, vol. 505 No. 7483, pp. 382-385.

Roy et al., "Triply-Responsive Boronic Acidblock Copolymers: Solution Self-Assembly Induced by Changes in Temperature, Ph, or Sugar Concentration", Chem. Commun. 2009, (16), 2106-2108.

Shi et al., "Recyclable 3d Printing of Vitrimer Epoxy", Mater. Horiz. 2017, vol. 4 No. 4, pp. 598-607.

Shirzaei Sani et al., "Sutureless Repair of Corneal Injuries Using Naturally Derived Bioadhesive Hydrogels", Sci Adv 2019, vol. 5 No. 3, eaav1281, pp. 1-14.

Wang et al., "Instant, Tough, Noncovalent Adhesion", ACS Appl. Mater. Interfaces 2019, vol. 11 No. 43, pp. 40749-40757.

Wang et al., "Recent Advances in Phenylboronic Acid-Based Gels with Potential for Self-Regulated Drug Delivery", Molecules 2019, vol. 24 No. 6, pp. 1-21.

Zhang et al., "Probing the Mechanism of Thermally Driven Thiol-Michael Dynamic Covalent Chemistry", Org. Biomol. Chem. 2018, vol. 16 No. 15, pp. 2725-2734.

* cited by examiner

AB$_{15}$C$_2$ hydrogel     MXene addition     Kneading     Composite

CONDUCTIVE HYDROGEL-BASED WEARABLE HEALTH MONITORS

CROSS-REFERENCE TO RELATED APPLICATIONS

This application claims priority to and the benefit of U.S. Provisional Application No. 63/365,284, "Conductive Hydrogel-Based Wearable Health Monitors" (filed May 25, 2022), the entirety of which foregoing application incorporated by reference herein for any and all purposes.

TECHNICAL FIELD

The present disclosure relates to the field of hydrogels and to the field of health monitors.

BACKGROUND

Existing skin-based sensing platforms for human health monitoring are typically composed of metallic, silicon, or hydrogel electrodes embedded in flexible silicone or plastic encapsulation. Although metals and silicon are conductive enough for general sensing purposes, they are stiff and rigid and tend to fail when the applied strain is greater than 3% in the case of silicon. Thus, they do not conform well to the complex contours of the human body. Furthermore, despite having good conductivity, oftentimes these materials still have quite high impedance when interfacing with the skin. Therefore, the electrode contacts need to be coated with electrolytic gels, which can irritate the skin. The gel will also dry out over time, resulting in poorer signal quality, and inability to record over long periods of time. Accordingly, there is a long-felt need in the art for improved electrode materials.

SUMMARY

In meeting the described long-felt needs, the present disclosure provides a health monitor, comprising: an electrode that includes a hydrogel composition comprising a first network that comprises at least two hydroxyl-bearing chains of a first polymer, the at least two hydroxyl-bearing polymer chains being crosslinked by crosslinks that comprise one or more boronic ester bonds; and at least one conductive additive dispersed within the composition, the electrode being configured for patient contact.

Also provided is a method, comprising operating a health monitor according to the present disclosure (e.g., according to any one of Aspects 1-21) to collect a signal of a subject.

Further provided is a method, comprising contacting the electrode of a health monitor according to the present disclosure (e.g., according to any one of Aspects 1-21) to a subject.

Additionally provided is a method, comprising releasing the electrode of a health monitor according to the present disclosure (e.g., according to any one of Aspects 1-21) to a subject.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various aspects discussed in the present document. In the drawings:

(FIG. 1A) Neat $AB_{15}C_2$ hydrogel, (FIG. 1B) dropping MXene solution directly on $AB_{15}C_2$ hydrogel, (FIG. 1C) mixing hydrogel and MXene through kneading, (FIG. 1D) conductive composite after kneading for 5 minutes.

(FIG. 2A) Bar plot of the DC conductivity of CHs with different types of conductive filler at the same loading percent (1 wt %). (FIG. 2B) Plot of the DC conductivity of a MXene-based CH at different loading of MXene by weight percentage. An equation of best fit is provided to demonstrate the relationship between conductivity and mass loading.

(FIG. 3A) Images of the CH-based epidermal electrodes in two different form factors. (FIG. 3B) Placement of hydrogel electrodes on the forearm of a health human subject. Note that standard clinical 3M 2360 electrodes have been placed as counter and reference electrodes along the forearm as well. (FIG. 3C, FIG. 3D) Bode plots showing the frequency response of the (FIG. 3C) impedance magnitude and (FIG. 3D) impedance phase for one subject, for a variety of epidermal electrodes.

DETAILED DESCRIPTION OF ILLUSTRATIVE EMBODIMENTS

Figures 1A, 1B, 1C, 1D:
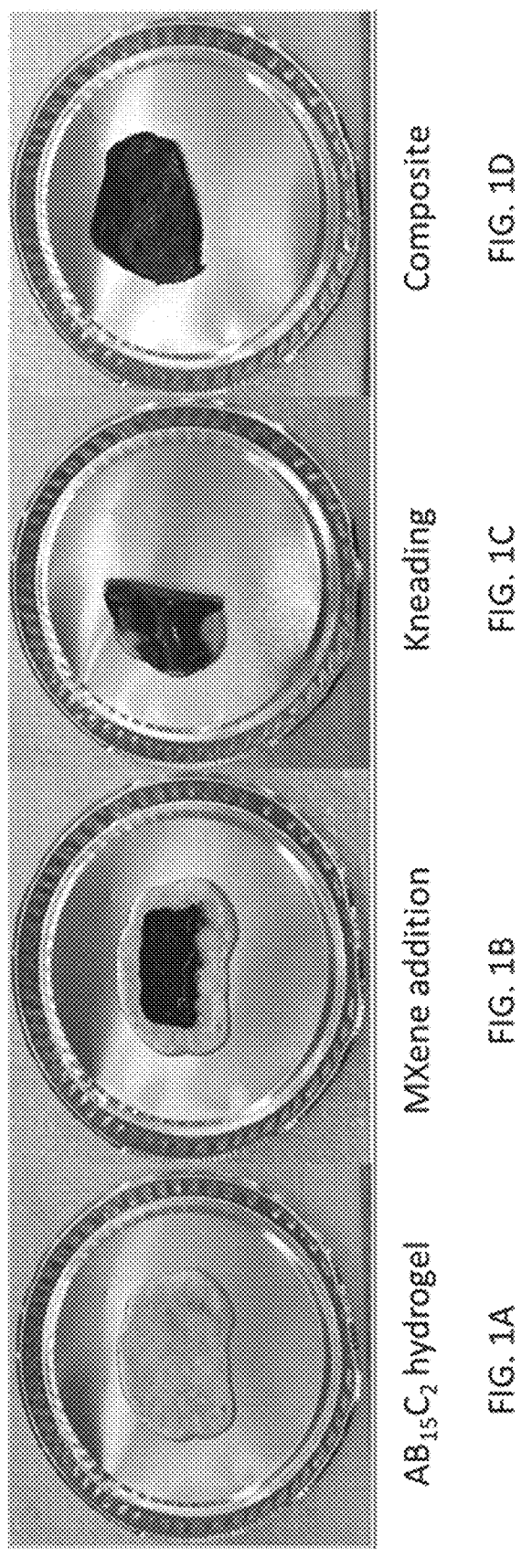
FIGS. 1A-1D illustrate fabrication of a composition according to the present disclosure. As shown, conductive filler is mixed into a base hydrogel, creating a conductive hydrogel (CH) that can then be patterned into the desired design.

The present disclosure may be understood more readily by reference to the following detailed description of desired embodiments and the examples included therein.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing. All publications, patent applications, patents and other references mentioned herein are incorporated by reference in their entirety. The materials, methods, and examples disclosed herein are illustrative only and not intended to be limiting.

The singular forms "a," "an," and "the" include plural referents unless the context clearly dictates otherwise.

As used in the specification and in the claims, the term "comprising" may include the embodiments "consisting of" and "consisting essentially of" The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any impurities that might result therefrom, and excludes other ingredients/steps.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

Unless indicated to the contrary, the numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently of the endpoints (e.g., "between 2 grams and 10 grams, and all the intermediate values includes 2 grams, 10 grams, and all intermediate values"). The endpoints of the ranges and any values disclosed herein are not limited to the precise range or value; they are sufficiently imprecise to include values approximating these ranges and/or values. All ranges are combinable.

As used herein, approximating language may be applied to modify any quantitative representation that may vary without resulting in a change in the basic function to which it is related. Accordingly, a value modified by a term or terms, such as "about" and "substantially," may not be limited to the precise value specified, in some cases. In at least some instances, the approximating language may correspond to the precision of an instrument for measuring the value. The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4. Further, the term "comprising" should be understood as having its open-ended meaning of "including," but the term also includes the closed meaning of the term "consisting." For example, a composition that comprises components A and B may be a composition that includes A, B, and other components, but may also be a composition made of A and B only. Any documents cited herein are incorporated by reference in their entireties for any and all purposes.

BACKGROUND

Most skin-based sensing platforms for human health monitoring are composed of metallic, silicon, or hydrogel electrodes embedded in flexible silicone or plastic encapsulation. While metals and silicon are conductive enough for general sensing purposes, they are stiff and rigid. They tend to fail when the applied strain is greater than 3% in the case of silicon. Thus, they do not conform well to the complex contours of the human body. Furthermore, despite having good conductivity, oftentimes these materials still have quite high impedance when interfacing with the skin. Therefore, the electrode contacts need to be coated with electrolytic gels, which can irritate the skin. The gel will also dry out over time, resulting in poorer signal quality, and inability to record over long periods of time.

To overcome these challenges, we formulate a conductive hydrogel (CH) that not only has low impedance, but is naturally adhesive, flexible, and stable for long-term health monitoring purposes. It is composed of a simple polyvinyl alcohol (PVA)-based hydrogel with dynamic covalent bonds and other biocompatible polymers such as chitosan, into which a variety of conductive fillers may be added, including carbon nanotubes (CNTs), PEDOT:PSS, and MXene. The disclosed CH is much cheaper to manufacture than the current epidermal electrodes. They may also perform better than current sensing platforms. The envisioned end product of this work would be a single-use disposable wearable electrode, which could be used for a few hours up to a few days of continuous health monitoring. The CH electrodes can also be used for implantable devices.

DISCLOSURE

Conductive hydrogels (CHs) have been recently explored for a variety of applications, including for wearable sensing applications. Many of the CH-based sensors have only been demonstrated for stress/strain sensing, though, when worn on the skin surface, or for drug delivery/release when implanted. In particular for wearable health monitoring applications, an electrode technology that could sense stress/strain, temperature, blood pressure, pulse and heart rhythms, and skin hydration could be a versatile tool for improving diagnostic care. CH-based epidermal sensors in particular may have many advantages over current state-of-the-art technologies because of their inherently good flexibility and their improved compatibility with the human body. Furthermore, the materials needed to realize a CH-based sensing technology are much cheaper than standard materials for epidermal sensing.

The types of conductive fillers typically used to make CHs are similar across publications: solutions-processable, carbon-based nanomaterials such as CNTs, PEDOT:PSS, and MXene are the most commonly used. As for the hydrogel itself, there can be a formulation of polyvinyl alcohol (PVA) or other polymer rich with hydroxyl groups along with boronic acid, forming a network with boronic ester bonds, which are a type of dynamic covalent bonds that can open and close upon activation by water or via shearing. Biocompatible materials such as acrylamide, sodium alginate, and chitosan and other polysaccharides such as dextran and sucrose can be added as additives to tune the mechanical properties of the gels.

One can mix conductive fillers (e.g., MXene, reduced graphene oxide (rGO), PEDOT:PSS, or CNTs) into a PVA-base hydrogel, resulting in a conductive hydrogel with highly advantageous properties for wearable health monitoring. The fabrication of the proposed CHs is simple and easily scalable, as it only involves mixing of the hydrogel base with the conductive filler of choice (FIGS. 1A-1D). Following mixing, electrodes can be easily fabricated for targeted needs.

Figures 2A, 2B:
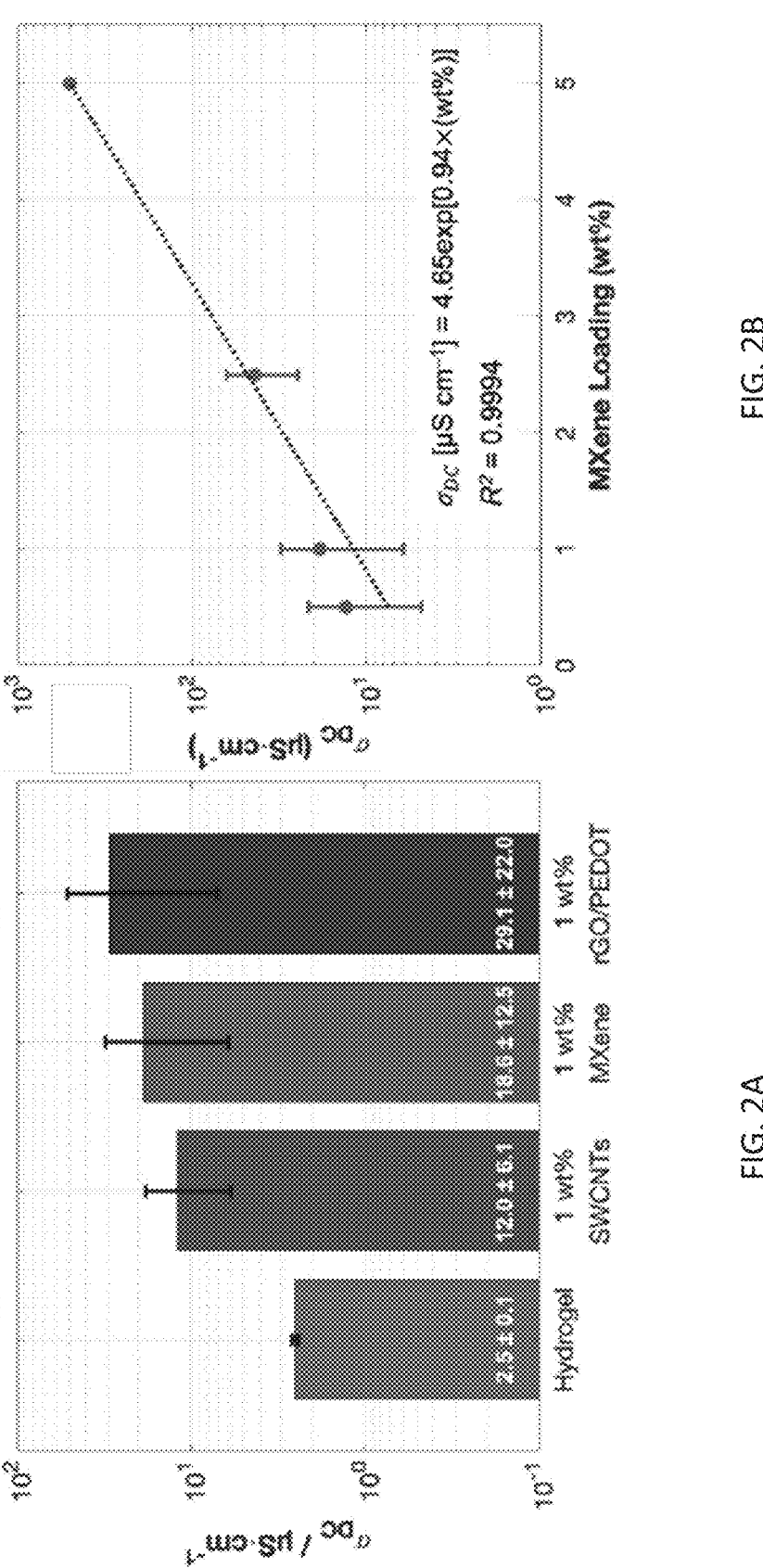
FIGS. 2A-2B.
Figure 3A:
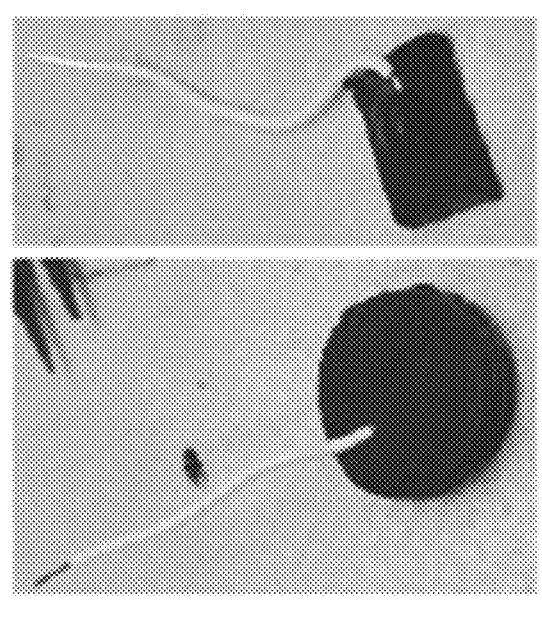
FIGS. 3A-3D.
Figure 3B:
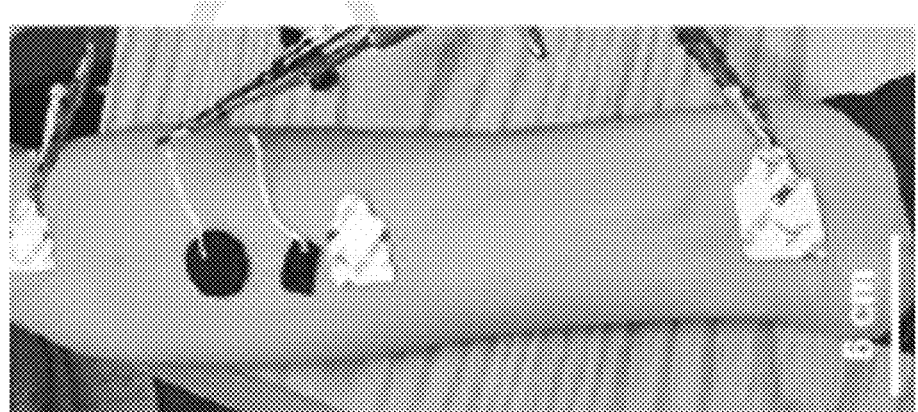
Figure 3D:
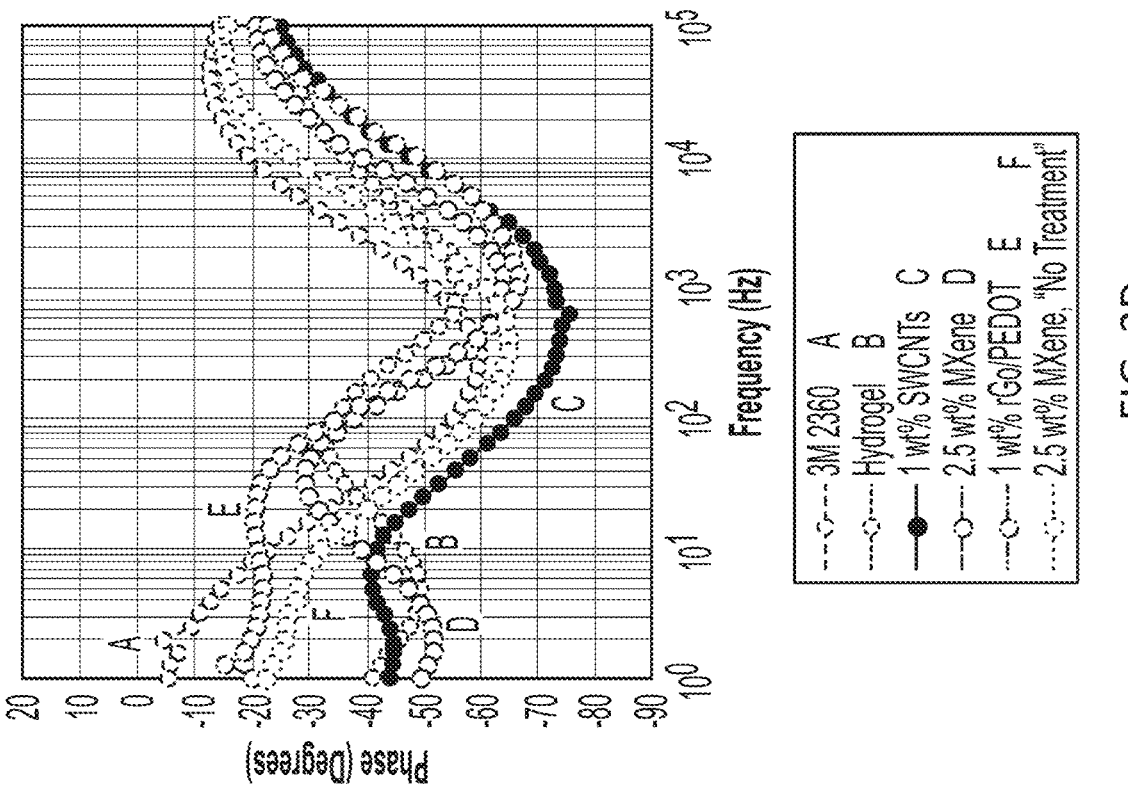
Figure 3C:
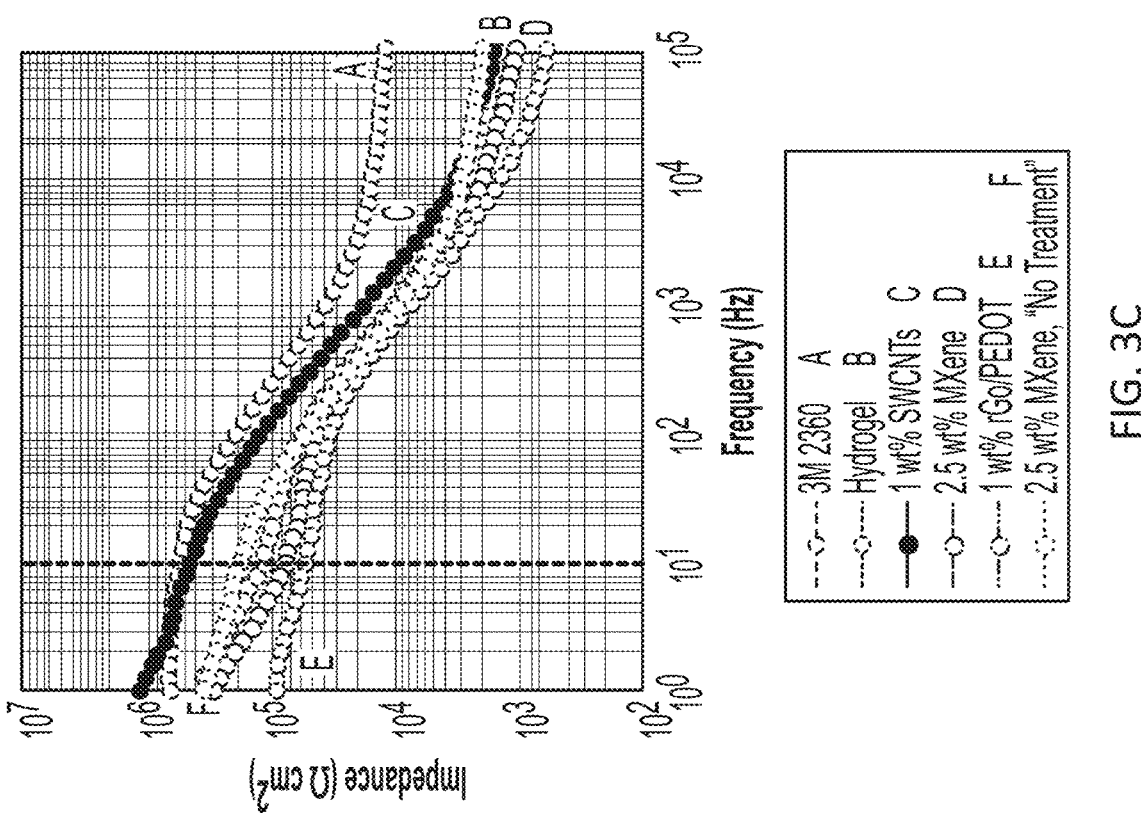

For a given application, one can select a suitable conductive filler, as well as determine how much of that filler is useful to boost the direct current (DC) conductivity of the resulting CH. As shown herein, we have that there can be a direct relationship between the conductivity and the filler loading, as shown in FIGS. 2A-2B.

Firstly, the starting conductivity of the hydrogel by itself is on par with the conductivity of water (2.5±0.1 µS cm-1), which is to be expected since the hydrogel itself is a water-inundated matrix. When adding conductive fillers, though, the conductivity can be boosted significantly depending on the filler of choice. Single-walled CNTs increase the conductivity by ~6× (12.0±6.1 µS cm$^{-1}$), while MXene—which is a more conductive nanomaterial than SWCNTs—boosts the hydrogel's conductivity by ~9× (18.6±12.5 µS cm$^{-1}$). It is also possible to incorporate additives—such as salts (e.g., NaCl, MgCl2, LiCl) or anti-oxidants (e.g., ascorbic acid, sodium ascorbate)—to the hydrogels when mixing with a given conductive filler, which may serve to further boost the conductivity. We have even explored combinations of conductive fillers, and found that mixing reduced graphene oxide (rGO) and PEDOT:PSS into the hydrogel boosted the final DC conductivity by an order of magnitude (29.1±22.0 µS cm-1). We also determined that there was a direct relationship between the conductive filler loading amount (controlled for by determining the weight percentage) and the final DC conductivity. For MXene alone, we were able to increase the DC conductivity by 2-3 orders of magnitude, simply by adding more material to the base hydrogel. Between 0.5 wt % and 5.0 wt % loading, we determined an exponential relationship between the mass loading and the DC conductivity. These results suggest that (i) the CHs provided in this disclosure are highly versatile and can be made from a wide variety of conductive materials; and (ii) the CHs provided in this disclosure have a fine-tunable conductivity, and so can likely be made to cater to specific applications.

We also explored the benefits of the CH structures in a mesoscale electrode format, in a preliminary skin impedance study (FIGS. 3A-3D). The goal was to compare the hydrogel skin impedance values to a clinical standard used for ECG recording—the 3M 2360 gelled Ag/AgCl electrodes. For this study, CH-based electrodes were made using the same variety of conductive fillers previously described in FIGS. 2A-2B. The electrodes were defined to have geometric surface areas of ~1-4 cm$^2$, and simple electrical wires were connected to the hydrogels to allow for connecting to a potentiostat. A healthy human subject was then recruited and their skin was cleaned with an isopropyl alcohol (IPA) swab. Subsequently, 3M TracePrep abrasive tape was used to lightly abrade the subject's skin-a standard skin intervention practice used for clinical EMG and ECG recording. After this skin treatment was applied, the various electrodes were placed and the skin impedance was measured. A Gamry Reference 600 potentiostat was used for epidermal impedance measurements, with 3M 2360 reference and counter electrodes placed at the subject's wrist and the pit of the elbow, respectively (see FIGS. 3A-3D). For the sake of comparison, we also recorded the skin impedance of a MXene-based CH electrode that was placed over a region of the subject's skin that did not receive any skin treatment beyond the initial skin cleaning.

Figure 4:
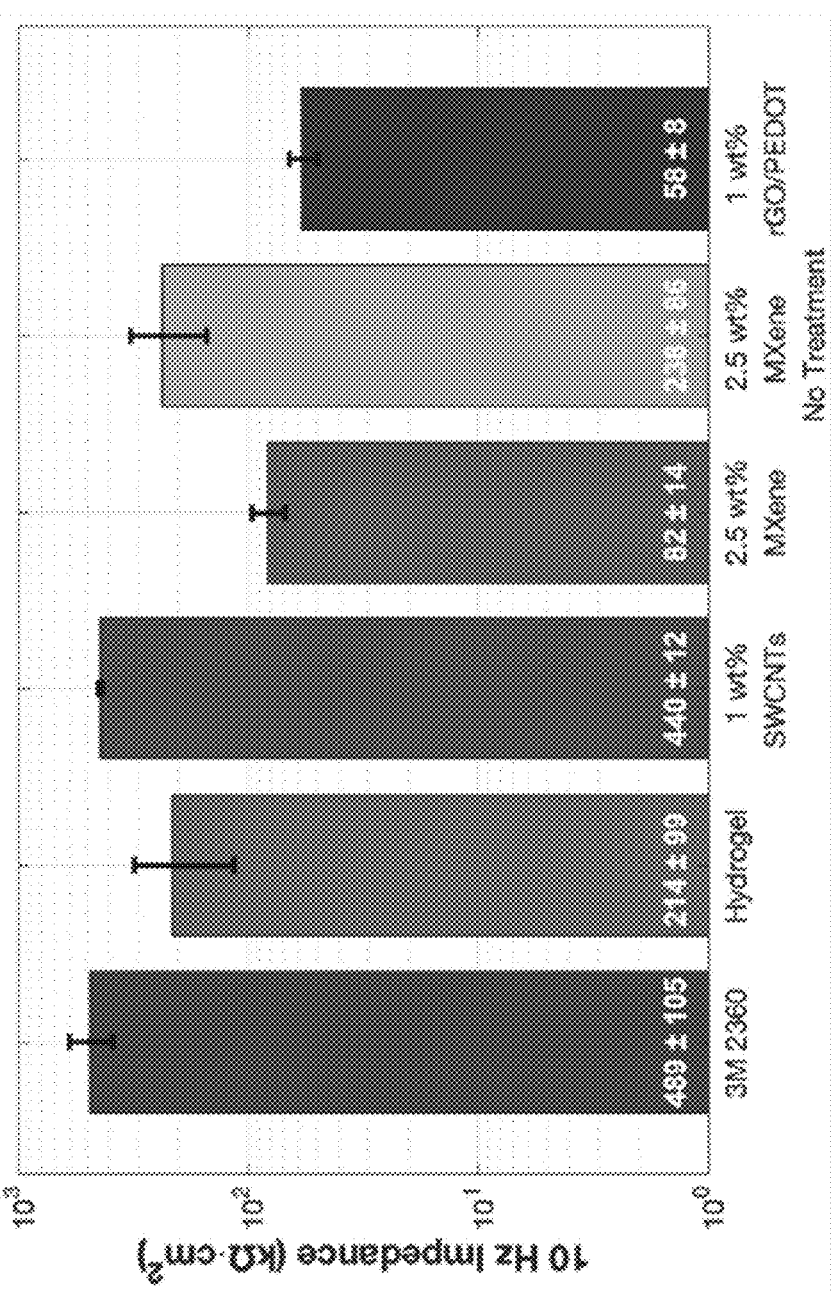
FIG. 4 Bar plot of the 10 Hz skin impedance of the CH-based electrodes, in comparison to a clinical standard (the 3M 2360 ECG electrodes). Bars represent means, error bars are std. dev. across N=2 subjects for all non-MXene samples, and N=3 subjects for the MXene samples.

FIGS. 3A-3D show the impedance spectra of the various CH-based electrodes after normalizing by the electrode surface area. All of the CH-based hydrogels have lower skin impedance than the 3M 2360 electrode. This is very encouraging, as the 3M 2360 is a standard clinical electrode for diagnostic ECG monitoring. The fact that the CH-based hydrogels have lower impedance than this clinical standard, then, suggests that this invention could be used for similar applications as the 3M 2360, and perhaps with better recording capabilities. At the 10 Hz reference frequency set by the ANSI AAMI EC12 Standard for ECG Electrodes, all the CH-based electrodes had lower impedance than the 3M 2360 electrode (FIG. 4). Interestingly, even the MXene-loaded CH electrode over skin without any treatment also had lower skin impedance than the 3M 2360. This suggests that this invention could even be used for epidermal diagnostics without the need for additional skin treatments, which increases safety and usability of the electrodes.

In summary, a conductive hydrogel-based wearable health monitor (CH-WHM) can be realized by simple mixing of a conductive filler with a basic PVA-based hydrogel. Mixing can be completed in a rudimentary way by hand, for simplest processing; however, more thorough loading may be achieved via shear mixing or continual folding of the hydrogel and conductive filler material. Further characterization will be necessary to ensure optimal percolation of the conductive filler into the hydrogel.

Conductive fillers (e.g., CNTs, MXenes, PEDOT:PSS) can be easily integrated into the base hydrogel to boost the overall conductivity of the CH-WHM, and the final conductivity of the CH-WHM can be controlled and/or fine-tuned according to the loading of conductive filler (e.g., wt %, mass %, vol %). CH-WHMs can be easily made from CHs via molding or other casting methods into any shape, and electrical connections can be directly made to CH-WHMs without the need for soldering or other forms of electrical wiring.

The skin impedance of CH-WHMs was found to be <500 kΩ cm$^2$ at 10 Hz, which is sufficiently low to record most skin-based biopotentials (e.g., ECG, EMG), and furthermore, the skin impedance of CH-WHMs may be lower than commercially available standards (e.g., 3M 2360), suggesting that CH-WHMs are not only cheaper to manufacture, but also may perform better than currently available technologies. An electrode that performs better on the skin surface may lead to improved diagnostics for patient care in the hospital. Finally, CH-WHMs may not need skin treatment to still have sufficiently low skin impedance for recording, which suggests that these devices can be easier to use without any particular skin treatment. This is an advantage particularly for recording from human populations with highly sensitive skin, such as neonates or the elderly.

Aspects

The following Aspects are illustrative only and do not limit the scope of the present disclosure or the appended claims. Any part or parts of any one or more Aspects can be combined with any part or parts of any one or more other Aspects.

Aspect 1. A health monitor, comprising: an electrode that includes a hydrogel composition comprising a first network that comprises at least two hydroxyl-bearing chains of a first polymer, the at least two hydroxyl-bearing polymer chains being crosslinked by crosslinks that comprise one or more boronic ester bonds; and at least one conductive additive dispersed within the composition, the electrode being configured for patient contact.

The electrode can be square, round, or other shape useful for clinical applications. The electrode can include a removeable (e.g., peelable) layer that is removed to expose at least a portion of the electrode for patient contact.

Aspect 2. The health monitor of Aspect 1, wherein the boronic ester bonds are derived from reaction between a boric acid or a boronic acid and a hydroxyl of the first polymer.

Aspect 3. The health monitor of any one of Aspects 1-2, further comprising an amount of boric acid, an amount of a boronic acid, or both.

Aspect 4. The health monitor of Aspect 3, wherein the boronic acid is one or more of phenylboronic acid, a phenylboronic acid derivative, a diboronic acid, a multiboronic acid, an aromatic boronic acid with a substitution, or any combination thereof.

Aspect 5. The health monitor of Aspect 3, wherein (i) the first polymer and the (ii) amount of boric acid, an amount of a boronic acid, or both are present in a weight ratio of from about 4:1 to about 50:1, optionally about 15:1. The ratio can be, e.g., from about 4:1 to about 50:1, from about 5:1 to about 45:1, from about 7:1 to about 42:1, from about 10:1 to about 40:1, from about 12:1 to about 38:1, from about 15:1 to about 35:1, from about 20:1 to about 30:1, or even about 25:1.

Aspect 6. The health monitor of any one of Aspects 1-3, wherein the at least one conductive additive comprises a carbon nanotube (including single-wall, double-wall, and multi-wall carbon nanotubes), a MXene, poly(3,4-ethylene-dioxythiophene) polystyrene sulfonate (PEDOT:PSS), graphene, graphene oxide, or any combination thereof.

A health monitor according to the present disclosure can also include multiple conductive additives, e.g., a first conductive additive and a second conductive additive. As a non-limiting example, a health monitor according to the present disclosure can include graphene flakes and carbon nanotubes. Without being bound to any particular theory or embodiment, the carbon nanotubes can function as bridges between the two-dimensional graphene flakes, thereby giving rise to a network of conductive additive within the health monitor. It should be understood, of course, that the foregoing example does not establish that graphene flakes cannot form a conductive network on their own. Instead, it should be understood that the presence of a second (or third, or other further) conductive additive can give rise to useful performance. A user can thus select the conductive additive (or additives) used in a given composition based on the user's own performance criteria.

As a further consideration, the choice of additive can affect the mechanical properties of the hydrogel composition. For example, the present of a given additive (or combination of additives) can give rise to a hydrogel composition that is comparatively stiff. Likewise, the presence of a given additive (or combination of additives) can give rise to a composition that is comparatively flexible.

Aspect 7. The health monitor of Aspect 6, wherein the at least one conductive additive is present at from about 0.1 to about 15 wt % (for example, from about 0.1 to about 15 wt %, from about 0.5 to about 12 wt %, from about 1 to about 10 wt %, from about 2 to about 9 wt %, from about 3 to about 8 wt %, from about 4 to about 7 wt %, from about 5 to about 6 wt %, and all intermediate values and sub-ranges) relative to the conductive hydrogel composition.

Aspect 8. The health monitor of Aspect 7, wherein the at least one conductive additive is present at from about 1 to about 5 wt % relative to the conductive hydrogel composition.

Aspect 9. The health monitor of any one of Aspects 1-8, wherein the first polymer comprises a polyol.

Aspect 10. The health monitor of Aspect 9, wherein the polyol comprises polyvinyl alcohol (PVA).

Aspect 11. The health monitor of any one of Aspects 1-10, further comprising a biocompatible additive.

Aspect 12. The health monitor of Aspect 11, wherein the biocompatible additive comprises a salt, polyacrylamide, a monosaccharide, a disaccharide, an oligosaccharide, a polysaccharide, or any combination thereof.

The choice of biocompatible additive can, in some instances, be driven by adjusting the conductivity of the hydrogel composition. Without being bound to any particular theory or embodiment, the presence of a salt can increase the conductivity of the hydrogen composition.

Aspect 13. The health monitor of Aspect 12, wherein the polysaccharide comprises chitosan, dextran, sodium alginate, or any combination thereof. Without being bound to any particular theory or embodiment, chitosan is a particularly suitable polysaccharide for use in the disclosed technology.

Aspect 14. The health monitor of Aspect 12, wherein the disaccharide comprises sucrose.

Aspect 15. The health monitor of any one of Aspects 11-14, wherein the biocompatible additive forms a second network. This can take place, e.g., with the use of chitosan as the biocompatible additive.

Aspect 16. The health monitor of Aspect 15, wherein the second network hydrogen bonds to the first network.

Aspect 17. The health monitor of any one of Aspects 1-16, further comprising an electrical lead in electronic communication with the electrode.

Aspect 18. The health monitor of any one of Aspects 1-17, wherein the composition exhibits a DC conductivity in the range of from about 10 to about 40 S/cm.

Aspect 19. The health monitor of any one of Aspects 1-18, wherein the composition exhibits an impedance, at 10 Hz, of less than about 500 k$\Omega$-cm$^2$ (e.g., from about 1 to about 490, from about 5 to about 450, from about 10 to about 400, from about 20 to about 350, from about 50 to about 350, from about 75 to about 300, or from about 100 to about 250 500 kQ-cm$^2$) in contact with abraded human skin.

Aspect 20. The health monitor of Aspect 19, wherein the composition exhibits an impedance, at 10 Hz, of from about 50 to about 450 kQ-cm$^2$ (for example, from about 50 to about 450, from about 75 to about 425, from about 100 to about 400, from about 125 to about 375, from about 150 to about 350, from about 175 to about 325, from about 200 to about 300, from about 225 to about 275, or even about 275 kQ-cm$^2$, and all intermediate values and sub-ranges) in contact with abraded human skin.

Aspect 21. The health monitor of any one of Aspects 1-20, wherein the composition exhibits an impedance, at 10 Hz, of less than about 240 kQ-cm$^2$ (for example, less than 240, 220, 200, 180, 160, 140, 120, 100, 80, 60, 40, or even 20 kQ-cm$^2$) in contact with untreated human skin.

Aspect 22. A method, comprising operating a health monitor according to any one of Aspects 1-21 to collect a signal of a subject.

Aspect 23. A method, comprising contacting the electrode of a health monitor according to any one of Aspects 1-21 to a subject.

Aspect 24. A method, comprising releasing the electrode of a health monitor according to any one of Aspects 1-21 from a subject. Release can be effected by, e.g., application of water or other aqueous media, changing pH (e.g., by application of buffer), temperature change, and the like. The releasing can be effected with an application of minimal or zero mechanical force, which in turn makes the disclosed technology especially suitable for applications to delicate tissues that are especially susceptible to mechanical force.

Aspect 25. The method of Aspect 24, wherein the releasing is effected by application of water.

It should be understood that the electrodes of the disclosed heath monitors can be pre-formed into a desired shape, e.g., an electrode disc. This is not a requirement, however, as an electrode can be formed in situ, i.e., at the location of use.

As a non-limiting example, a user can apply an amount of hydrogel-forming material to a use location (e.g., a user's scalp) so that the hydrogel conforms to the use location. This can present an advantage over pre-formed electrodes in that an electrode formed in situ can achieve particularly close contact with the use location. This can be especially beneficial for use locations where hair can be present (e.g., the user's scalp), as the hydrogel-forming material can flow around the hair and achieve close contact with the patient's scalp. A user can use a barrier to control the flow of hydrogel-forming material, e.g., a ring or other mold placed at the use location.

The disclosed technology can be deployed externally (e.g., to the scalp), but can also be deployed internally. As an example, an electrode according to the present disclosure could be applied directly to a patient's muscle or brain tissue. Because the disclosed electrodes can be released by stimuli (e.g., application of water) other than application of mechanical force, the disclosed electrodes can be used internally in locations for which traditional adhesive-based electrodes are not well-suited.

What is claimed:

1. A health monitor, comprising:
   an electrode that includes a hydrogel composition comprising a first network that comprises at least two hydroxyl-bearing chains of a first polymer,
   the at least two hydroxyl-bearing polymer chains being crosslinked by crosslinks that comprise one or more boronic ester bonds; and
   at least one conductive additive dispersed within the hydrogel composition to form a conductive hydrogel composition,
   the electrode being configured for patient contact.

2. The health monitor of claim 1, wherein the boronic ester bonds are derived from reaction between a boric acid or a boronic acid and a hydroxyl of the first polymer.

3. The health monitor of claim 1, further comprising an amount of boric acid, an amount of a boronic acid, or both.

4. The health monitor of claim 3, wherein the boronic acid is one or more of phenylboronic acid, a phenylboronic acid derivative, a diboronic acid, a multiboronic acid, an aromatic boronic acid with a substitution, or any combination thereof.

5. The health monitor of claim 3, wherein (i) the first polymer and the (ii) amount of boric acid, an amount of a boronic acid, or both are present in a weight ratio of from about 4:1 to about 50:1.

6. The health monitor of claim 1, wherein the at least one conductive additive comprises a carbon nanotube, a MXene, poly(3,4-ethylenedioxythiophene) polystyrene sulfonate (PEDOT:PSS), graphene, graphene oxide, or any combination thereof.

7. The health monitor of claim 6, wherein the at least one conductive additive is present at from about 0.1 to about 15 wt % relative to the conductive hydrogel composition.

8. The health monitor of claim 7, wherein the at least one conductive additive is present at from about 1 to about 5 wt % relative to the conductive hydrogel composition.

9. The health monitor of claim 1, wherein the first polymer comprises a polyol.

10. The health monitor of claim 9, wherein the polyol comprises polyvinyl alcohol (PVA).

11. The health monitor of claim 1, further comprising a biocompatible additive.

12. The health monitor of claim 11, wherein the biocompatible additive comprises a salt, polyacrylamide, a monosaccharide, a disaccharide, an oligosaccharide, a polysaccharide, or any combination thereof.

13. The health monitor of claim 12, wherein the polysaccharide comprises chitosan, dextran, sodium alginate, or any combination thereof.

14. The health monitor of claim 12, wherein the disaccharide comprises sucrose.

15. The health monitor of claim 11, wherein the biocompatible additive forms a second network.

16. The health monitor of claim 15, wherein the second network hydrogen bonds to the first network.

17. The health monitor of claim 1, further comprising an electrical lead in electronic communication with the electrode.

18. The health monitor of claim 1, wherein the composition exhibits a DC conductivity in the range of from about 10 to about 40 S/cm.

19. The health monitor of claim 1, wherein the conductive hydrogel composition exhibits an impedance, at 10 Hz, of less than about 500 $k\Omega$-$cm^2$ when adapted to contact abraded human skin.

20. The health monitor of claim 19, wherein the conductive hydrogel composition exhibits an impedance, at 10 Hz, of from about 50 to about 450 $k\Omega$-$cm^2$ when adapted to contact abraded human skin.

21. The health monitor of claim 1, wherein the conductive hydrogel composition exhibits an impedance, at 10 Hz, of less than about 240 $k\Omega$-$cm^2$ when adapted to contact untreated human skin.

22. A method, comprising operating a health monitor according to claim 1 to collect a signal of a subject.

23. A method, comprising contacting the electrode of a health monitor according to claim 1 to a subject.

24. A method, comprising releasing the electrode of a health monitor according to claim 1 from a subject.

25. The method of claim 24, wherein the releasing is effected by application of water.

* * * * *